(12) United States Patent
Sørensen et al.

(10) Patent No.: US 9,176,057 B2
(45) Date of Patent: Nov. 3, 2015

(54) APPARATUS AND METHOD FOR MEASURING RETROREFLECTIVITY OF A SURFACE

(75) Inventors: Kaj Sørensen, Kongens Lyngby (DK); Asbjørn Mejnertsen, Kokkedal (DK); Jan Harries Hansen, Kongens Lyngby (DK); Hans Ole Nielsen, Kongens Lyngby (DK)

(73) Assignee: DELTA DANSK ELEKTRONIK, LYS & AKUSTIK, Horsholm (DK)

( * ) Notice: Subject to any disclaimer, the term of this patent is extended or adjusted under 35 U.S.C. 154(b) by 0 days.

(21) Appl. No.: 13/576,044

(22) PCT Filed: Feb. 4, 2011

(86) PCT No.: PCT/EP2011/051682
§ 371 (c)(1),
(2), (4) Date: Nov. 20, 2012

(87) PCT Pub. No.: WO2011/095605
PCT Pub. Date: Aug. 11, 2011

(65) Prior Publication Data
US 2013/0194565 A1    Aug. 1, 2013

(30) Foreign Application Priority Data
Feb. 4, 2010    (DK) .................................. 2010 70040

(51) Int. Cl.
*G01N 21/55*    (2014.01)
(52) U.S. Cl.
CPC .......... *G01N 21/55* (2013.01); *G01N 2021/551* (2013.01)

(58) Field of Classification Search
None
See application file for complete search history.

(56) References Cited

U.S. PATENT DOCUMENTS

| 4,097,751 | A | * | 6/1978 | Egan et al. ............... 250/559.01 |
| 4,368,982 | A | * | 1/1983 | Van Arnam et al. .......... 356/445 |
| 4,721,389 | A |  | 1/1988 | Dejaiffe |
| 6,166,813 | A | * | 12/2000 | Roberts ........................ 356/445 |
| 6,212,480 | B1 | * | 4/2001 | Dunne .......................... 702/159 |
| 7,417,738 | B2 | * | 8/2008 | Taylor et al. .................. 356/445 |
| 2002/0186865 | A1 |  | 12/2002 | Retterath et al. |
| 2007/0171431 | A1 |  | 7/2007 | Laflamme |
| 2010/0316252 | A1 | * | 12/2010 | Burgoa Roman et al. .... 382/100 |

FOREIGN PATENT DOCUMENTS

| DE | 19850270 A1 | 5/1999 |
| EP | 1486799 A2 * | 12/2004 |
| EP | 2159568 A1 * | 3/2010 |
| EP | 2369323 A1 * | 9/2011 |
| FR | 2661248 A1 * | 10/1991 |

(Continued)

*Primary Examiner* — Gordon J Stock, Jr.
(74) *Attorney, Agent, or Firm* — Lisa V. Mueller; Michael Best & Friedrich LLP

(57) ABSTRACT

An apparatus for measuring the retroreflectivity of a surface. The apparatus comprises a light source for illuminating an area of said surface at an incident angle relative to the surface; a detector for detecting light reflected back from the surface at an observation angle relative to the surface; a signal processing unit adapted to receive a detector signal from the detector and to determine, from at least the received detector signal, a measure of retro reflectivity of the surface; a range finder for measuring a distance between the apparatus and the illuminated area. The signal processing unit is further adapted to adjust the measure of retroreflectivity responsive to the measured distance.

17 Claims, 3 Drawing Sheets

(56) References Cited

FOREIGN PATENT DOCUMENTS

| GB | 2067748 | A | * | 7/1981 |
| GB | 2372314 | A | | 8/2002 |
| WO | 00/06970 | A1 | | 2/2000 |
| WO | WO 2014076324 | A1 | * | 5/2014 |

* cited by examiner

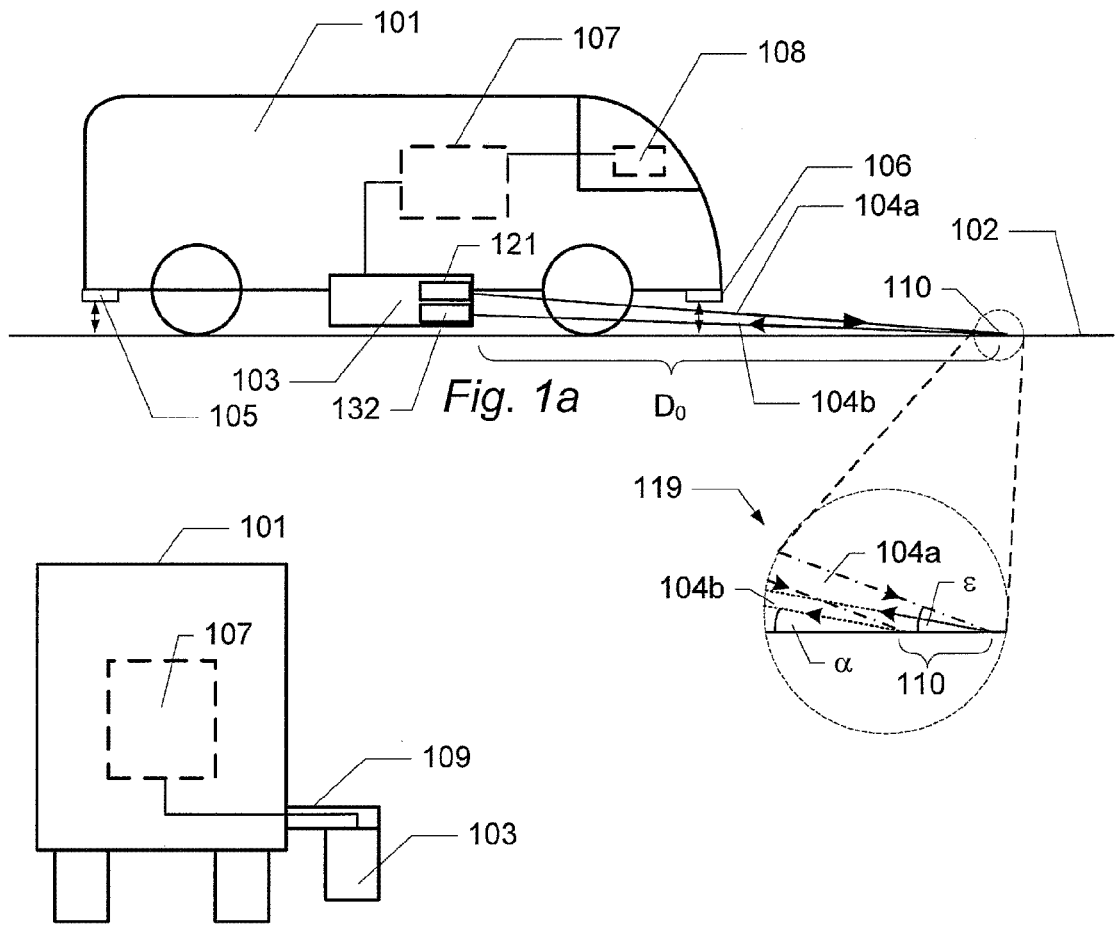
Fig. 1a
Fig. 1b
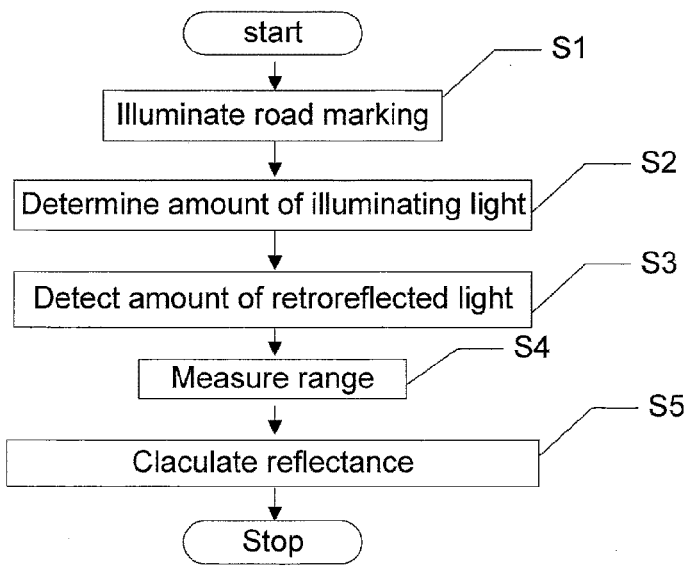
Fig. 2

APPARATUS AND METHOD FOR MEASURING RETROREFLECTIVITY OF A SURFACE

CROSS-REFERENCE TO RELATED APPLICATIONS

This is the U.S. national stage entry of International Patent Application No. PCT/EP2011/051682, filed on Feb. 4, 2011, which claims priority to Danish Patent Application No. PA 2010 70040, filed on Feb. 4, 2010, the contents of all of which are herein fully incorporated by reference.

FIELD OF THE INVENTION

The invention generally relates to an apparatus and method for measuring retroreflectivity of a surface. More particularly, the invention relates to an apparatus and method for measuring retroreflectivity of a layer of material applied to a surface, such as a road marking applied to a road.

BACKGROUND

Road markings are typically provided by application of marking materials such as paint, thermoplastic materials, cold hardening materials, preformed lines, and symbols onto the surface of the road. Road marking materials can be applied with or without addition of colors, e.g. white, yellow, or other colors.

Road markings are often profiled to produce a certain surface texture to enhance special properties, e.g. for enhancing retroreflectivity under conditions of wet or rainy weather, or to produce a signal to the driver of a vehicle in the form of an acoustistic signal or vibration when crossed at high speed.

In particular road markings may comprise addition of retro-reflective materials such as glass beads, in particular road markings intended for illumination by vehicle headlamp illumination.

U.S. Pat. No. 4,721,389 discloses a retroreflectivity measuring system that measures performance data relating to a reflective surface, such as a highway stripe or marking containing reflective glass beads. A laser beam illuminates a portion of the reflective surface with radiation of a predetermined wavelength, the laser being incident on the surface at an incidence angle i. The incident laser beam is then reflected back, at least partially, at a particular observation angle o that is separated from the incidence angle by a divergence angle delta. A telephotomultiplier aimed at the illuminated area receives the reflected laser beam at the observation angle o. The laser and the telephotomultiplier may be mounted on a servo-motor driven frame in order to scan the target area from a moving vehicle. Because the intensity of the incident beam is fixed and known, the measured intensity of the reflected laser light in the reflected beam can be used directly for providing a measure of the retroreflectivity of the reflective surface.

Even though the above prior art system provides a measure of the retroreflectivity of a roadmarking, it remains a problem to improve the accuracy of the measurements, in particular when the measurements are performed from a moving vehicle.

SUMMARY

Disclosed herein is an apparatus and corresponding method for measuring a measure of retroreflectivity of a surface such as the surface of a reflective layer applied to a road or other surface. Embodiments of the apparatus comprise:

a light source for illuminating an area of said surface at an incident angle relative to the surface;

a detector for detecting light reflected back from an observation area of the surface at an observation angle relative to the surface;

a signal processing unit adapted to receive a detector signal from the detector and to determine, from at least the received detector signal, a measure of retroreflectivity of at least a part of the surface;

wherein the apparatus comprises at least one device for measuring a distance between the apparatus and the illuminated area; and wherein the signal processing unit is further adapted to adjust the measure of retroreflectivity responsive to the measured distance.

Consequently, the effect of variations of the distance between the illuminated area of the surface and the apparatus on the measured reflectivity is reduced or even eliminated, thereby increasing the accuracy of the measurement.

In particular, when the apparatus is mounted on a vehicle or otherwise used to perform measurements while moving across the surface, the distance between the illuminated area of the surface and the apparatus may change during the measurement or between consecutive measurements. For examples, when the vehicle with the apparatus mounted to it moves along a road, the inclination of the vehicle relative to the surface of the road may change, e.g. due to an uneven road, driving through a curve, a shifting load of the vehicle, movements of the driver and/or passengers. Furthermore, since the road may not be completely plane but include inclines, the distance at which the illuminating beam hits the road surface may change over time.

The distance between the apparatus and the illuminated area may be a distance between a suitable reference location of the apparatus and a suitable reference point of the illuminated area. Examples of suitable reference locations of the apparatus include the position of the detector, of the light source, of an aperture, of a lens, or of any other component of the optical system of the apparatus. Examples of suitable reference points of the illuminated area include a geometric centre of the illuminated area, an edge of the illuminated area, or the like. For example, the signal processing unit may be adapted to determine a measure of retroreflectivity of a part of the illuminated area of the surface, e.g. a part imaged on or otherwise detected by an element or group of elements (e.g. corresponding to a pixel or group of pixels of an image) of a detector array or by an otherwise defined position of a position-sensitive detector; the detected distance may thus be a distance between the apparatus and said part of the illuminated area.

The device for measuring the distance may include any suitable device or circuitry for directly determining a distance and/or for determining any other suitable quantity such as an angle from which a distance can be determined. Examples of suitable devices for measuring the distance include range finders e.g. range finders utilising an active method (such as sonar, laser, or radar) for measuring the distance; other examples include devices that measure the distance using trigonometry, e.g. stadiametric range finders and parallax, or coincidence range finders. Some examples of range finders may use a set of known distances or target sizes to make the measurement.

In some embodiments, the device for measuring the distance may be embodied by the light source, the detector and the signal processing unit, thus providing an integrated unit that allows both the measurement of reflected amounts of light and the measurement of the distance to the point of reflection using a single light source and detector pair, thereby reducing the complexity and production costs of the apparatus.

In some embodiments, the detector comprises a position-sensitive detector for detecting light as a function of a position within a light receiving area, wherein the signal processing unit is adapted to determine the distance from a position within the light receiving area of the detected light reflected back from the surface.

For the purpose of the present description, the term retroreflectivity is intended to refer to the relative amount of light reflected from a surface in a direction generally back toward the light source emitting the light that illuminates the surface and is reflected back. An amount of light may e.g. be measured in lux. A suitable measure of retroreflectivity of a field of a surface is the coefficient of retroreflected luminance $R_L$, measured in candlepower reflected light per square meter of apparent area of the field per lux incident light at the field measured perpendicular to the illumination direction (candelas per square meter per lux). Even though retroreflectivity is generally concerned with light reflected in a direction generally back toward the light source emitting the incident light, it will be appreciated that there may be certain angular differences between the observation angle and the incident angle. Retroreflectivity at specified incident angles and observation angles are frequently quoted as parts of specifications for retroreflective surfaces. However, it will be appreciated that other measures of retroreflectivity may be used in connection with embodiments of the apparatus and method disclosed herein.

The light source may be any suitable light source for emitting light at one or more suitable wavelength(s) or range(s) of wavelengths, e.g. visible light, at which the retroreflective properties of a surface are to be determined. Examples of suitable light sources include a laser, a flash lamp, one or more light-emitting diodes, and/or the like. The light source may further comprise an optical system for directing light emitted by the light source as a light beam incident onto the surface, e.g. a focussed or collimated light beam. The incident light is then at least partially reflected by the surface in a direction generally back toward the apparatus, at least partially at a particular observation angle.

The illuminated area may have any suitable shape and size. For example, the illuminated area may be a spot, an elongated stripe, or the like. The position of the illuminated area may be fixed relative to the apparatus or it may vary, e.g. by moving the illuminated area across the retroreflective surface area. In some embodiments, the illuminated area may have a linear extent in at least one direction that is larger than the linear extent of the retroreflective surface in that direction, such that the illuminated area extends across the retroreflective surface as well as across a surface area surrounding the retroreflective surface and having different retroreflective properties, e.g. a smaller or even substantially no retroreflection. The observation area from which light is detected by the detector may be larger than the illuminated area, thereby allowing a detection of the position of the illuminated area within the observation area.

The detector may be any suitable circuitry or device for detecting light at the wavelength(s) or in the wavelength range(s) at which the light is reflected back from the surface. Examples of suitable detectors include a position-sensitive detector that detects an amount of light as a function of the position within a light receiving one-dimensional or two-dimensional detection field, such as detector arrays, e.g. one- or two-dimensional detector arrays, such as a CCD chip, or the like. When the detector is configured to detect an image of the illuminated area of the surface, the signal processing unit may process the detected image so as to determine additional properties of the surface, such as the geometry of a retroreflective portion of the surface and/or a contrast of the retroreflective portion relative to a non-retroreflective portion of the surface surrounding the retroreflective portion. In general, the observation area may comprise at least a part of the illuminated area; the observation area may be larger than the illuminated area or smaller than the illuminated area. In some embodiments the observation area is a spot, and array of spots, a moving spot, and/or the like.

In some embodiments, the signal processing unit further receives data indicative of the emitted amount of light, e.g. an amount of light emitted toward the illuminated area. The signal processing unit may thus calculate the measure of reftroreflectivity from the detector signal and the data indicative of the emitted amount of light. In one embodiment, the apparatus comprises an optical system for directing a predetermined portion of the emitted light to the detector, thus providing a reference signal indicative of the amount of emitted light. Hence, in this embodiment, the detector signal includes information of both the emitted and the measured reflected amount of light, thus allowing an accurate and efficient computation of the measure of retroreflectivity. When the optical system of the apparatus directs the predetermined portion, e.g. an image of an aperture of the light source, of the emitted light to a first position on a position-sensitive detector, such as detector array, and the optical system further directs the at least a portion of the retroreflected light (e.g. an image of said illuminated area of the surface) to a second position, different from the first position, of the position-sensitive detector, the amounts of the emitted and retroreflected light may be measured simultaneously. This allows an efficient and accurate calculation of the reflectance, and a calculation in real time.

The processing unit may scale the measure of retroreflectivity by computing a scaled measure of retroreflectivity as a suitable scaling function from at least the measured distance and from a quantity from which the measure of retroreflectivity is computable, e.g. the measured amount of reflected light, or the retroreflectance itself. For example, the signal processing unit may calculate the scaled measure of retroreflectivity as the raw measure multiplied by a suitable scaling factor. The scaling factor may include, or be equal to, a function of the ratio of the measured distance and a baseline or nominal distance. In one embodiment the scaling factor is a function of the ratio squared. In one embodiment, the scaling factor is equal to the ratio squared.

It will be appreciated that the apparatus and method described herein may be used to measure retroreflective properties of surfaces that are exposed to ambient light such as daylight.

Examples of a signal processing unit include any circuit and/or device suitably adapted to determine a measure of retroreflectivity from at least the received detector signal. In particular, the above term comprises general- or special-purpose programmable microprocessors, Digital Signal Processors (DSP), Application Specific Integrated Circuits (ASIC), Programmable Logic Arrays (PLA), Field Programmable Gate Arrays (FPGA), special purpose electronic circuits, programmable logic controllers (PLC) etc., suitably programmed computers or other data processing systems, or a combination thereof.

The different aspects of the present invention can be implemented in different ways including the apparatus and the method described above and in the following and further systems and/or product means, each yielding one or more of the benefits and advantages described in connection with at least one of the aspects described above and in the following, and each having one or more preferred embodiments corresponding to the preferred embodiments described in connection with at least one of the aspects described above and in the following and/or disclosed in the dependant claims. Furthermore, it will be appreciated that embodiments described in connection with one of the aspects described herein may equally be applied to the other aspects.

Embodiments of the apparatus described herein may be used for measuring a retroreflective property of road markings, e.g. from a moving vehicle. For example, the apparatus may be mounted to a vehicle, such that the apparatus illuminates an area of the surface of the road in front or behind of the vehicle.

Further embodiments and advantages are disclosed below in the description and in the claims. Embodiments of the apparatus described herein allow an accurate measurement of the retroreflectivity properties of a surface while the apparatus is moved across the surface, e.g. at a predetermined height above the surface. Embodiments of the apparatus described herein allow a measurement of further parameters of the surface, such as the geometry and/or contrast of retroreflective portions of the surface, e.g. of portions covered by a layer of retroreflective material such as a road marking.

In some embodiments the apparatus described herein is adapted to perform the measurement of the retroreflectivity according to one or more international standards, such as EN 1436. Accordingly, in some embodiments, the light source is a broadband light source. The detector may have a sensitivity corresponding to the sensitivity of the human eye.

In some embodiments the illumination area has a predetermined shape and size and a well-defined edge. For example, the illumination area may have a rectangular or trapezoid shape. The apparatus is operable to determine from a captured image of the illumination area the distance between the apparatus and the illumination area by means of a triangulation operation, and to adjust the received signal such that it corresponds to a signal as if received from a predetermined distance, e.g. a distance prescribed in an international standard.

BRIEF DESCRIPTION OF THE DRAWINGS

The invention will now be described more fully below with reference to the drawings, in which FIGS. 1a-b schematically show an embodiment of an apparatus for measuring retroreflectivity of road markings.

FIG. 2 shows a flow diagram of a process for measuring retroreflectivity of road markings.

DETAILED DESCRIPTION

Figure 3:
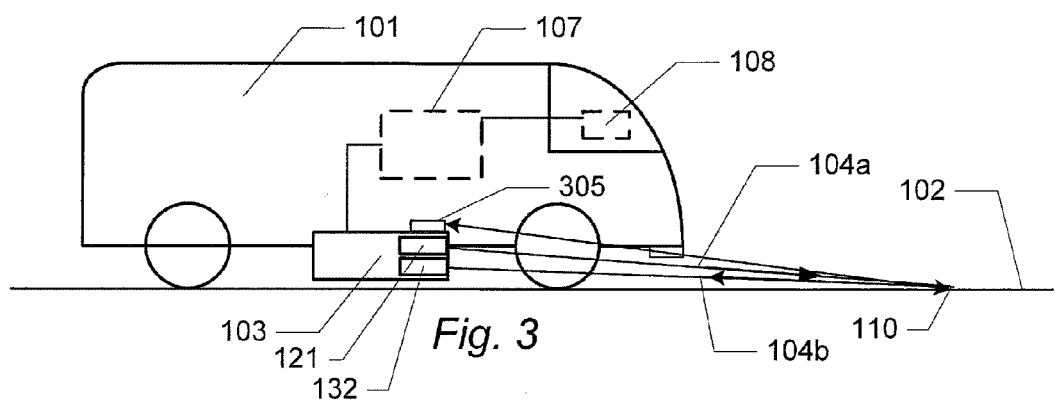
FIGS. 3-4 schematically show other embodiments of an apparatus for measuring retroreflectivity of road markings.

FIGS. 1a-b schematically show an embodiment of an apparatus for measuring retroreflectivity of road markings. The apparatus comprises an illumination and detection unit 103 and a signal processing unit 107. In the example of FIGS. 1a-b the illumination and detection unit is mounted to the side of a vehicle 101, while the signal processing unit 107 is located inside the vehicle. It will be appreciated that in alternative embodiments both the illumination and detection unit 103 and the signal processing unit 107 may be integrated into a single unit.

FIG. 1a shows a side view of the vehicle 101, e.g. a car, truck, or the like, while FIG. 1b shows a rear view of the vehicle.

The illumination and detection unit 103 is mounted to the side of the vehicle 101 via a suitable frame 109 at a predetermined height above the surface 102 of the road. The illumination and detection unit is aligned with, or at an angle with, the forward direction of the vehicle, and at a suitable lateral distance from the co-driver side of the vehicle, such that the vehicle can conveniently be maneuvered along a road with the illumination and detection unit aligned above a line of road markings. It will be appreciated that the illumination and detection unit may alternatively be mounted at a different position of the car, e.g. the driver's side, in front of the car, or even behind the car.

The illumination and detection unit 103 comprises an illumination unit 121 including a light source (not explicitly shown in FIGS. 1a-b) and a detector unit 132. The illumination and detection unit is arranged to emit a light beam 104a in the forward direction of the vehicle such that the light beam hits the surface 102 of the road at a position 110 at a predetermined nominal distance $D_0$ in front of the apparatus (e.g. as measured from the output aperture of the apparatus). The illumination and detection unit 103 detects the retroreflected light 104b that is generally reflected back into the illumination and detection unit. In the enlarged section 119 of the area around the illuminated area 110 of the surface of the road, the incident light beam 104a and the portion 104b of the retroreflected light that is detected by the illumination and detection unit 103 under observation angle $\alpha$ are shown in more detail. Generally there may be a small difference between the illumination angle $\epsilon$ of the incident light beam 104a and the observation angle $\alpha$ under which the retroreflected light 104b is detected.

When the frame is adjustable (e.g. by means of adjusting screws or other suitable adjustable mounting mechanism) such that the height of the apparatus above the ground and/or the vertical and/or horizontal adjustment/inclination of the emitted light beam may be adjusted, the position and orientation of the illumination and detection unit may easily be adjusted so as to calibrate the illumination and detection unit to illuminate the surface 102 at a predetermined incident angle $\alpha$ and a predetermined nominal distance from the apparatus.

The detector unit 132 and the illumination unit 121 may be aligned such that their respective optical axes are in the same vertical halfplane.

In the example shown in FIG. 1, the detector unit is positioned below (i.e. closer to the surface than) the illumination unit. This arrangement will also be referred to as inverted arrangement, as it is different from the normal arrangement in which the detector unit 132 is placed above the illumination unit 121. The normal arrangement may be seen as representing driving in a vehicle with the headlamps of the vehicle placed lower than the eyes of the driver. The normal arrangement corresponds to relevant measurement standards such as EN 1436 and ASTM E 1710 that define a standard measuring geometry with an observation angle $\alpha$ of 2.29° and an illumination angle $\epsilon$ of 1.24°. The normal arrangement leads to direct measurement of the intended retroreflectivity value $R_L$.

Placement of the detector unit 132 below the illumination unit 121 provides the inverted arrangement which leads to measurement of a modified retroreflectivity value $R_L^*$. The relationship between the two values is $R_L=(\sin \epsilon/\sin \alpha)\times R_L^*$. A measure of the intended retroreflectivity value $R_L$ may thus be obtained from a measurement of $R_L^*$ using the inverted arrangement by inserting the values for $\epsilon$ and $\alpha$ used during the measurement in the above expression, i.e. by $R_L=(\sin 1.24°/\sin 2.29°)\times R_L^*=0.542\times R_L^*$ in the case of the above-mentioned standard measuring geometry.

It has turned out that the modified retroreflectivity value $R_L^*$ is much less sensitive to those offsets of the angles that occur in practical measurements due to movements of the vehicle during driving, than the intended retroreflectivity value $R_L$. The inverted arrangement has, therefore, the advantage that it provides more accurate measurements. It can be seen in the way that the normal arrangement involves measurement of the ratio $\sin \epsilon/\sin \alpha$, which varies, while this is avoided in the inverted arrangement.

For the inverted arrangement, the measured luminance is higher than for the normal arrangement. This is reflected by the use of the factor 0.542 to downscale the modified retroreflectivity value $R_L^*$ to the intended retroreflectivity value $R_L$ for the above-mentioned standard geometry. The cause is actually that when illuminating at the larger of the two angles the illuminance of the surface as measured on the plane of the surface is also higher. This in itself leads to more accurate measurements by higher signals and better competition with signals from foreign light, in particular daylight.

The above-mentioned standards allow for a larger aperture of the unit that is placed highest (at the angle of 2.29°) than of the unit placed lowest (at the angle of 1.24°). The inverted arrangement has, therefore, the further advantage that it may provide even higher signals and further improvement of the accuracy compared to the normal arrangement.

The apparatus may optionally comprise a user interface unit 108 allowing the operator of the apparatus to control the apparatus and/or monitor the measurements online during operation. The interface unit 108 may be integrated into the signal processing unit 107 or be embodied as a separate unit. For example, the interface unit may be located in the driver's cabin of the vehicle 110. When the adjustment means of the frame 109 are controllable via the interface unit 108, the illumination and detection unit 103 my easily be aligned by the operator from the driver's cabin, i.e. under the same load conditions of the vehicle as during subsequent operation. For example, the adjustable mounting mechanism may be activated by one or more electrical motors, e.g. servo motors, a pneumatic and/or hydraulic system, or in any other suitable way allowing remote control of the adjustable mounting mechanism.

Generally, the apparatus further comprises a device for measuring the actual distance D between the illumination and detection unit 103 and the illuminated area 110 during actual operation of the apparatus, as this distance may vary during operation and thus differ from the nominal distance $D_0$. In the example of FIGS. 1 *a-b*, the device for measuring the actual distance D comprises two distance sensors 105 and 106, respectively, e.g. laser-based range finders, that measure the height of the undercarriage (or another suitable reference point) of the vehicle to the surface 102 of the road at two different locations, e.g. the front and the rear of the vehicle. The measured heights are then fed into the signal processing unit 107 which determines the inclination of the vehicle relative to the surface, and computes an estimate of the distance D between the illumination and detection unit 103 and the illuminated area 110. For example, this calculation may be based on an initial calibration measurement in combination with an initial adjustment of the height and inclination of the illumination and detection unit 103. For example, the operator may, after adjustment of the illumination and detection unit 103, manually measure and enter the distance D, and perform a calibration measurement of the distances by the range finders 105 and 106. The measured and entered calibration values may thus be stored in the signal processing unit and used for subsequent calculation of the distance based on measurements by the range finders 105 and 106.

FIG. 2 shows a flow diagram of a process for measuring retroreflectivity of road markings, e.g. as performed by one of the apparatus of FIGS. 1*a-b*, 3 and 4. In step S1, the apparatus is controlled by the signal processing unit 107 or a separate control unit, to direct a light beam onto an area of the surface of the road which comprises the road marking. The generated light beam may be a collimated or focussed beam illuminating a predetermined area on the surface of the road, e.g. an elongated stripe extending across a portion of a road marking. Road markings are often provided as stripes extending in the direction of the road. The illumination and detection unit may thus be arranged to illuminate a stripe extending across a road marking in a transversal direction of the road marking. In alternative embodiments, the illumination and detection unit may provide a light beam, e.g. a laser beam, or other narrowly collimated beam that transversally scans across a road marking. In some embodiments the beam is focussed onto a spot or line/stripe on the road at a nominal distance $D_0$ away from the illumination and detection unit 103. For example, the nominal distance may depend on the height above the surface of the road at which the illumination and detection unit is mounted, and on the desired incident and observation angles. For example, the nominal distance may be between 2 m and 10 m, e.g. between 4 m and 8 m, such as between 5 m and 7 m, e.g. 6 m.

In step S2, the signal processing unit receives information about the amount of light illuminating the illuminated area to be measured. For example, if the intensity of the light source is sufficiently constant over time and sufficiently uniform across the illuminated area, the amount of the illuminating light may be determined during an initial calibration, e.g. by directing the light beam onto a surface with known reflectivity and by measuring the corresponding detected signal. If the amount of illuminating light varies across the illuminated area of the surface, a plurality of calibration values may be determined for respective portions of the illuminated area of the surface. The measured values may thus be stored in the signal processing unit 107 for use as reference values during subsequent retroreflectivity measurements. Alternatively or additionally, if the amount of illuminating light varies over time, the calibration process may have to be repeated and/or the amount of light may be measured for during operation, e.g. for each measurement to be performed. In some embodiments, the spatial distribution of the illuminating amount of light across the illuminated area of the surface may be measured in connection with each measurement. A suitable apparatus and method for such a measurement will be described in greater detail below.

In step S3, the illumination and detection unit 103 measures the amount of light reflected back from the illuminated area of the surface of the road. To this end, the detector may be a one-dimensional array of detector elements that is scanned in a direction transversal to the direction of the one-dimensional array, so as to detect light reflected back from a predetermined area on the surface of the road. Alternatively, the detector may be a two-dimensional array of detector elements. In some embodiments, the illumination and detection unit is configured to obtain an image of the surface area of the road focussed at the nominal distance $D_0$. The illumination and detection unit forwards the detected light intensity, or the detected intensities detected by the detector elements of the one- or two-dimensional detector array to the signal processing unit 107.

In step S4, the apparatus determines the actual distance D between the illuminated area of the surface of the road and the illumination and detection unit 103. The distance may be determined by a number of different methods as is described in more detail in connection with FIGS. 1a-b, 3 and 4. The measured actual distance D is also forwarded to the signal processing unit 107.

In step S5, the signal processing unit 107 computes the retroreflectance of the illuminated area from the received or stored reference value(s), the determined actual distance D, and the detected amount(s) of retroreflected light. For example, the signal processing unit may calculate the retroreflectance R as the fraction of a measured amount of retroreflected light divided by a corresponding reference value indicative of the amount of light incident onto the area of the retroreflecting surface from which the amount of retroreflected light has been detected. The signal processing unit further scales the calculated reflectance value by a suitable scaling function $f_{scaling}$ computed from the measured actual distance D to obtain a scaled reflectance $R_{scaled}$, e.g. according to $$R_{scaled} = f_{scaling}(D) \cdot R = f_{scaling}(D) \cdot I_{retroreflected}/I_{reference},$$

In particular, in the case of a focussed light beam, focussed at a predetermined nominal distance $D_0$ from the illumination and detector unit, the signal processing unit 107 may multiply the retroreflectance by a scaling factor determined as the ratio squared of the actual and the nominal distance to obtain a scaled retroreflectance according to $$R_{scaled} = (D^2/D_0^2) \cdot R.$$

For example, the above calculation may be performed for each detector element, e.g. for each pixel of an acquired image, thus resulting in a retroreflectance value for each pixel which subsequently may be averaged. Consequently, the signal processing unit 107 corrects the measured retroreflectance for errors caused by the fact that the actually illuminated area of the surface of the road may lie at a distance different from the nominal distance due to movements of the vehicle on which the illumination and detection unit is mounted, due to an uneven and/or inclined road surface, and/or the like.

The signal processing unit may store the computed scaled reflectance values, e.g. in association with data indicating the place and/or time of measurement, e.g. GPS data indicating the position of the vehicle at the time of measurement. Alternatively or additionally, the calculated reflectance values may be displayed on a user interface 108 of the apparatus.

An example of the above process will be described in further detail with reference to the illumination and detection unit of FIG. 5 below. It will be appreciated that the signal analysis performed by the signal processing unit may be performed in real-time, thus allowing the operator to monitor the measurement results during operation. Alternatively or additionally, the measured raw data may be stored on a suitable storage medium, thus allowing subsequent off-line analysis by the signal processing unit 107 or an external data processing system.

Figure 4:
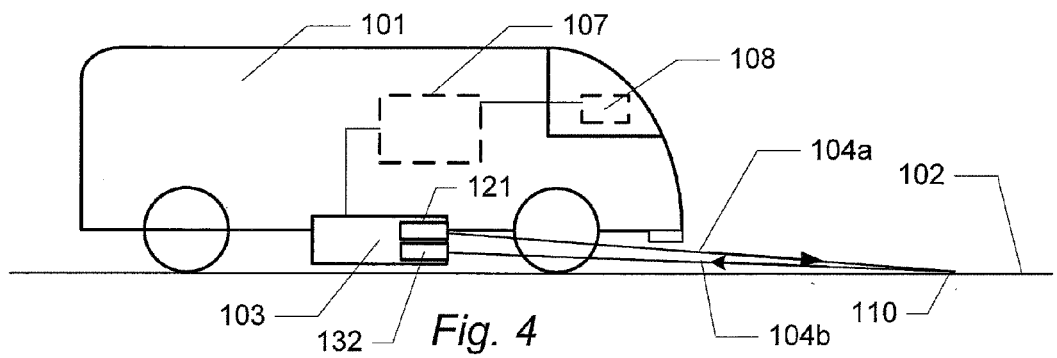

FIGS. 3-4 schematically show other embodiments of an apparatus for measuring retroreflectivity of road markings. The embodiments shown in FIGS. 3 and 4 are similar to the embodiment described with reference to FIGS. 1 a-b, and they only differ from the embodiment of FIGS. 1a-b and from each other by the type of device for measuring the distance D used.

The apparatus of FIG. 3 uses a single range finder 305, e.g. a conventional laser-based range finder, which is configured to directly measure the distance from the illumination and detection unit 103 to the illuminated area 110.

In the embodiment of FIG. 4, the device for measuring the distance D is integrated into the illumination and detection unit 103. In this embodiment, the distance between the illumination and detection unit 103 and the illuminated area 110 is measured by means of the retroreflected light detected by the illumination and detection unit 103. To this end, the illumination and detection unit 103 may comprise a position-sensitive detector that detects retroreflected light from an observation area that is larger than the illuminated area. Examples of suitable combinations of observation areas and illuminated areas are illustrated in FIGS. 6-9 below.

Figure 5:
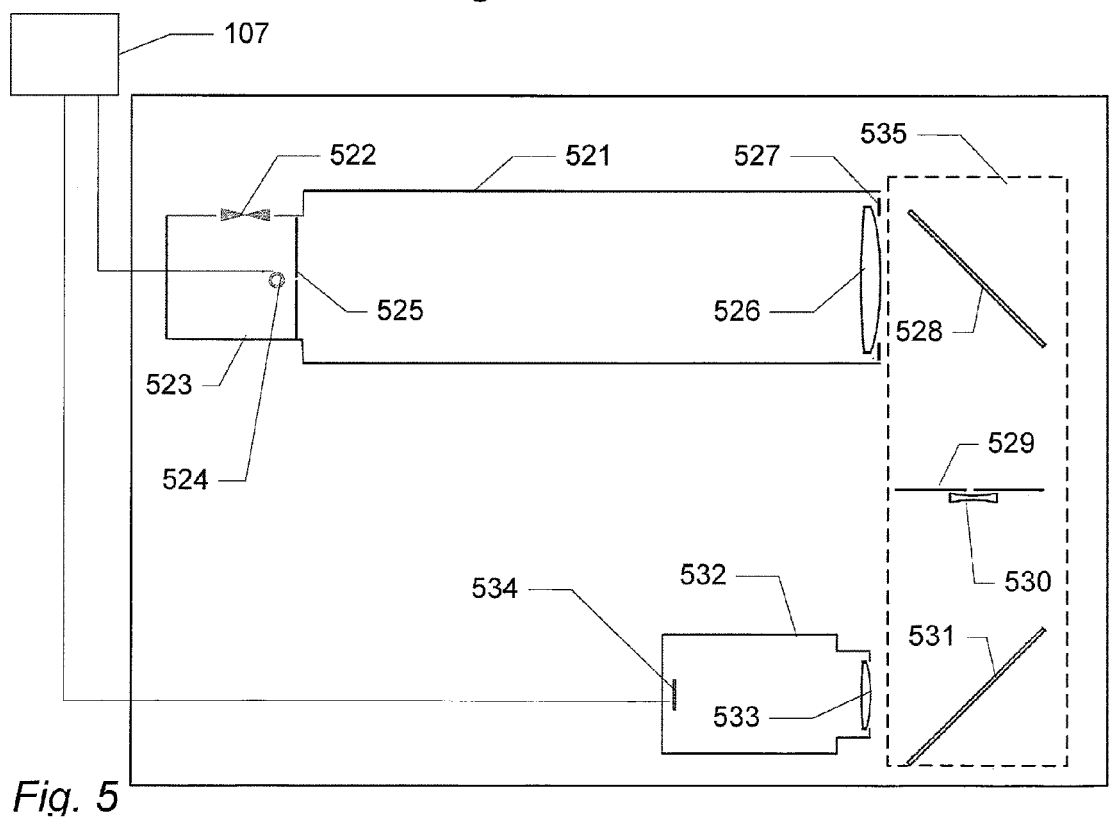
FIG. 5 schematically shows an embodiment of an apparatus for measuring retroreflectivity of road markings in more detail.

FIG. 5 schematically shows an embodiment of an apparatus for measuring retroreflectivity of road markings in more detail. In particular, FIG. 5 shows an embodiment of the illumination and detection unit suitable for use in any of the apparatus shown in FIGS. 1a-b, 3, and 4. The illumination and detection unit 103 of FIG. 5 comprises an illumination module 521, redirection optics 535, and a detector unit 532.

The illumination unit 521 comprises a lamp housing 523 comprising the light source 524, e.g. a lamp, and a fan 522 or other cooling device for ensuring that the lamp 524 is kept at a suitable operating temperature. For example, the lamp may be a Hereaus Noblelight xenon flash lamp, or another suitable flash lamp. For example, the lamp may be controlled to provide 25 flashes pr. second. Each flash may have a duration of e.g. 7 μs.

Generally, when the light source is configured to illuminate the illuminated area by short flashes, the illuminated area may be illuminated area may be illuminated by a high light intensity. Furthermore, when the detector is configured to detect the retroreflected light both during a flash and before or after a flash, i.e. without illumination from the light source, the signal processing unit may perform a compensation of the detected amount of retroreflected light for ambient light based on measurements for the same (or at least nearly the same) illuminated area. Alternatively or additionally, a compensation for ambient light may be performed based on measurements of the retroreflected light during a flash both from within the illuminated area and from another part of the retroreflective surface (e.g. another part of the same road marking) outside the illuminated area. This has the advantage the both measurements may be performed simultaneously. For example, the reflected light from the illuminated area and from an area outside the illuminated area may be determined from signals from different parts of the detector array, e.g. different parts of an exposed image.

In one embodiment, the detector may determine retroreflected light from the illuminated area and from a reference area that has a different distance from the measuring device than the illuminated area, but otherwise laterally aligned with the illuminated area. For example the reference area may be a stripe parallel with an illuminated stripe, but at a different distance. In one embodiment, the reference area is chosen to be positioned at a distance such that the distance between the observation area and the illumination area is at least approximately equal to the distance travelled by the vehicle carrying the measuring device between two measurements, e.g. between two exposures, or an integer multiple of that distance. Hence, a correction for ambient light may be performed based on a measurement of the (unilluminated) reference area in one image and a measurement of the illuminated area in another image taken at a different time. Due to the movement of the vehicle between these two measurements, the compensation will thus be based on measurements of the same part of the surface of the road. If the reference area is chosen at a larger distance than the illuminated area, the compensation may thus be performed based on a measurement of the reference area in one image and a measurement of the illuminated area in a subsequent measurement.

The illumination unit further comprises an illumination optical system for forming a focussed illumination beam. The optical system comprises a lamp aperture 525, a lens 526 or lens system, and an output aperture 527. For example, the lamp aperture may be an elongated slit which is imaged by the lens 526 at the nominal distance $D_0$; hence the illumination unit creates an elongated illuminated stripe on the road surface, preferably a stripe that is larger than the width of the road markings to be measured, e.g. at least 1 m wide so as to allow the operator to align the vehicle such that at least a portion of the illuminated stripe covers the road marking. For example, the lamp aperture may have a width of 30 mm and a height of 1.1 mm. Accordingly, the lens 526 may be a lens with a focal length of 150 mm which images the aperture 525 at a distance of $D_0$ from the illumination and detection unit. The output aperture may be a quadratic aperture, e.g. having a 35×35 mm$^2$ opening or another suitable aperture.

The redirection optics 535 comprises a first beam splitter 528, e.g. a glass plate, for redirecting a fraction of the focussed output beam from the illumination module via an aperture 529, and a lens 530 to a beam combiner 531, e.g. a second glass plate, into the detector module 532. For example, the beam splitter and beam combiner may each be a glass plate, e.g. 0.5 mm thick glass plate. The lens 530 may be a concave lens with a focal length of −3 m. The aperture 529 may be a pinhole of e.g. 1 mm diameter. Hence, the redirection optics creates an image of the lamp aperture on the detector chip 534.

The detector module 532 comprises a detector chip 534 and a focussing lens 533 for imaging an object onto the detector. The focussing lens has a focal length such that it images the detector 534 on a focal plane in a distance of the nominal distance $D_0$. For example, the detector module may be a CMOS camera of the type Dalse Falcon 1.4M100 with a lens of e.g. 50 mm focal length, and an aperture of 2.8. The CCD chip may have a width of about 10.5 mm each line including 1400 pixels, and a height of about 7.7 mm each column including 1024 pixels. The detector unit may be operated to capture images at a rate and duration synchronised with the flashes of the light source, e.g. with an exposure time set larger than the duration of the flashes, such as 10 µs in the case of 7 µs flashes.

In use, the lamp is controlled by the signal processing unit 107 or a separate control unit, to generate flashes at regular intervals. The emitted light is focussed on the road marking, nominally at a distance of $D_0$ from the illumination and detection unit. The detector module is configured to obtain images of the surface area of the road focussed at the nominal distance $D_0$ and synchronised with the flashes. Each image includes the illuminated area. Furthermore, the redirection optics causes a fraction of the emitted light to be redirected to the detector module such that the lens aperture 526 is also imaged on the detector chip 534.

Consequently, for each flash, the detector captures an image of the surface of the road including the stripe of light generated by the focussed beam from the illumination unit, i.e. the detector captures an image of the lamp aperture reflected by the road surface; this image will also be referred to as the retroreflected image. Simultaneously, the detector captures an image of the lamp aperture directly via the redirection optics; this image will also be referred to as reference image.

The captured images are forwarded to the signal processing unit 107 for further processing. The processing unit detects the actual stripes in the reference and retroreflected images, e.g. by means of conventional edge detection algorithms, optionally using a prior knowledge about the geometry of the stripes. Similarly, the processing unit detects the edges of the road marking. In one embodiment, the lens aperture generates horizontal stripes on the detector, while the road markings are substantially vertical stripes in the detected image.

It will be understood that each part (e.g. each pixel) of the retroreflected image of the lamp aperture may be associated with a corresponding part (e.g. a corresponding pixel or number of pixels) of the reference image of the lens aperture such that the associated parts are images of the same part of the lens aperture. Accordingly, the processing unit associates each pixel or group of pixels of the retroreflected image of the lens aperture with the corresponding pixel or group of pixels of the redirected image of the lens aperture. The signal processing unit further divides the detected light intensity of a pixel or group of pixels in the retroreflected image by the detected light intensity of the associated pixel or group of pixels of the redirected image, so as to compute local reflectance values for each pixel or group of pixels which subsequently may be averaged so as to obtain an average reflectance value.

The signal processing unit further scales each computed reflectance value by the ratio squared of the actual distance between the illumination and detection unit and the area of the surface illuminated by the image of the lamp aperture, and the corresponding nominal distance $D_0$. To this end, the signal processing unit determines the actual distance from the position of the retroreflected stripe on the detector array, using trigonometric relations.

In order to determine actual distance, a first exposure is made on a vertical reference surface, for instance a white board, placed perpendicular to the main measuring direction at the nominal distance $D_0$. Based on this calibration measurement, the signal processing unit determines the lower and upper edges of the stripe of light in terms of x and y-coordinates in the detector array. These are represented as two parallel lines:

lower edge of the stripe of light:

$$y = a_0 \cdot x + b_0$$

upper edge of the stripe of light:

$$y = a_0 \cdot x + b_0 + c_0.$$

These data are stored by the signal processing unit and are valid as long as the optics of the apparatus are not changed. For increased accuracy in the determination of the data, the first exposure may actually be the average of several exposures. It will be appreciated that the above calibration measurement may also be used to calibrate other parameters of the system. For example, the system may determine any deviation from a uniform illumination and/or deviation from a uniform detection across the reference surface, an adjustment of the focus of the optical system, etc.

In each exposure on roads, the signal processing unit determines the lower and upper edges of the stripe of light and represent them as two parallel lines:

lower edge of the stripe of light:

$$y = a \cdot x + b$$

upper edge of the stripe of light:

$$y = a \cdot x + b + c$$

The distance D at each element can now be obtained by $$D=1/(A+Bx+Cy)$$

where $$A=1/D_0+g\times(b\times c_0-b_0\times c)$$

$$B=g\times(a\times c_0-a_0\times c)$$

and $$C=g\times(c-c_0)$$

The factor g is given by $$g=\delta/(c\times h)$$

where $\delta$ is the angular distance between the directions of neighbouring elements
and h is the vertical distance between the units of observation and measurements.

These expressions are based on some approximations, among else that all relevant angles are small. They have been proved sufficiently accurate in practical use. The actual calculations are carried out by the signal processing unit.

The scaled reflectance values may then be averaged over the entire road marking and/or used to analyse the distribution of retroreflectivity over a road marking.

One the distance along the road is determined for each element, lateral distances can also be determined from the distances expressed in elements, when multiplying with the distance along the road, and with the angular distance between the directions of neighbouring elements. The signal processing unit determines in fact a complete mapping of the road within the exposure, including angles, and uses those to derive a multitude of information.

Because of this, it will be appreciated that the signal processing unit may perform alternative or additional computations, e.g. so as compensate for ambient light and/or to suitably calibrate the results and/or to compute alternative or additional quantities, such as a measure of contrast, geometry of the road marking, position and alignment of the apparatus etc.

In addition to the above reflectance values, the illumination and detection unit of FIG. 5 allows the determination of additional data from the captured images. For example, from the detected edges of the road markings, the size (in particular the width) of the road markings may be determined. Similarly, as the illumination beam illuminates both the road marking and surrounding parts of the road surface, a measure of the contrast of the road marking may be determined by comparing an amount of light reflected from the road marking and an amount of light reflected from the adjacent unmarked road surface that lies within the illumination stripe detected on the detector array.

FIGS. 6-9 illustrate respective examples of combinations of different illumination and detector geometries, generated by an illumination and detection unit as described herein, e.g. one of the illumination units shown in FIGS. 1a-b, 3, and 4.

Figure 6:
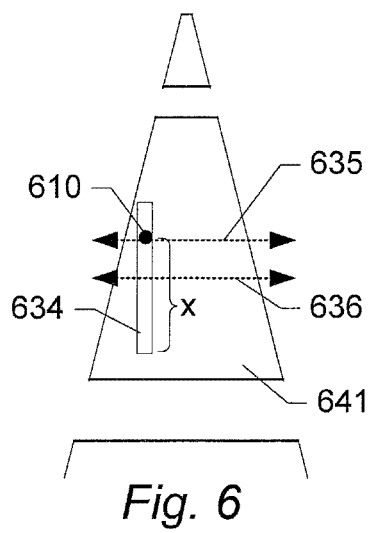
FIGS. 6-9 illustrate respective examples of combinations of different illumination and detector geometries.

In particular, FIG. 6 schematically shows a perspective view of a road marking 641 as seen from the illumination and detection unit. Furthermore, FIG. 6 shows an illuminated area 610 in the form of a small spot, e.g. as generated by a laser beam or other collimated or focused light beam. FIG. 6 further shows the observation area 634 of a one-dimensional detector array. During operation, the laser beam and the detector array may be controlled to laterally scan across the road marking as illustrated by arrows 635 and 636, respectively. The detector array extends in a direction orthogonal to the scanning direction. When the observation area 634 of the detector array and the illuminated spot 610 simultaneously scan across the road marking, the retroreflected light from the illuminated spot can be detected by the detector array in its observation area 634. Furthermore, the signal processing unit may determine the distance from the illumination and detection unit to the illuminated spot from the position (e.g. the x-coordinate) of the detected spot on the one-dimensional array.

Figure 7:
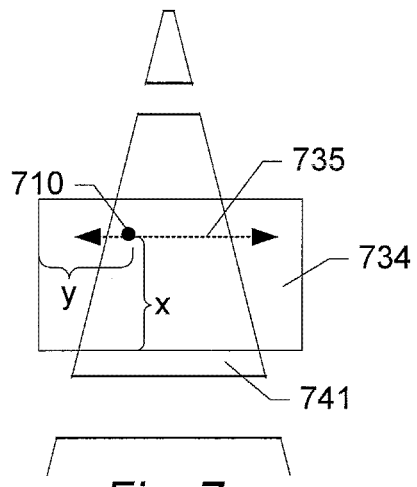

FIG. 7 schematically shows a perspective view of a road marking 741 as seen from the illumination and detection unit. Furthermore, FIG. 7 shows an illuminated area 710 in the form of a small spot similar to the illuminated spot 610 of FIG. 6. As above, during operation the illuminated spot 710 scans across the road marking as described in connection with FIG. 6. However, in this example, the one-dimensional detector array is replaced by a two-dimensional detector array corresponding to a two-dimensional observation area 734. The two-dimensional detector array may thus track the position of the illuminated spot without the need to move the detector array. To this end the lateral dimension and resolution of the detector arrays and the optical imaging system are configured such that the observation area covered by the detector array is covers the scanning range of the illuminated spot. As in the example of FIG. 6, based on the position of the detected illuminated spot 710 within the detector array (e.g. as determined by the x- and y-coordinates), the signal processing unit may determine the distance from the illumination and detection unit to the illuminated spot.

Figure 8:
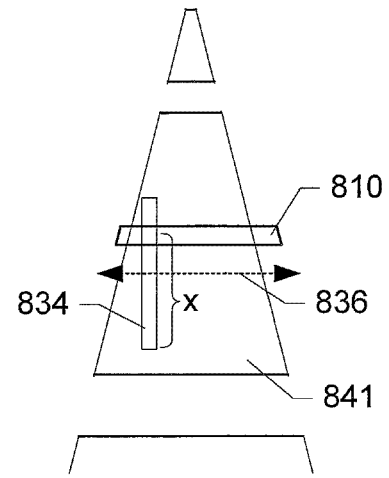

FIG. 8 schematically shows a perspective view of a road marking 841 as seen from the illumination and detection unit. Furthermore, FIG. 8 shows the observation area 834 of a one-dimensional detector array that is scanned across the road marking 841. In the example of FIG. 8, the illuminated spot is replaced by a stationary illuminated stripe 810 (or an illuminated area having a different geometry), e.g. as produced by the illumination and detection unit described with reference to FIG. 5. As in the above example, the signal processing unit may determine the distance from the illumination and detection unit to the illuminated stripe from the position (e.g. the x-coordinate) of the detected part of the stripe on the one-dimensional array.

Figure 9:
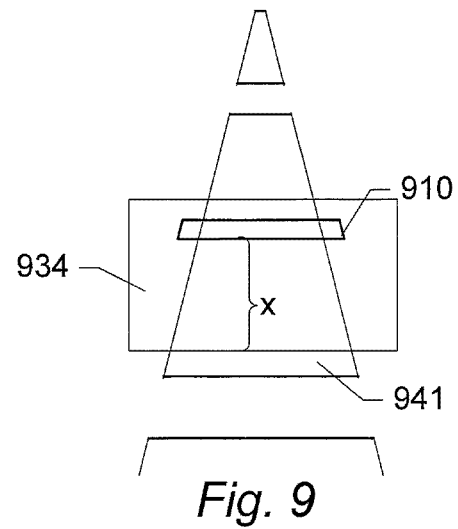

Finally, FIG. 9 illustrates an illuminated stripe 910 and the observation area 934 of a two-dimensional detector. Similar to the example of FIG. 7, based on the position of the detected illuminated stripe 910 within the detector array (e.g. as determined by the x- and y-coordinates), the signal processing unit may determine the distance from the illumination and detection unit to the illuminated spot. Hence, in this embodiment, an entire image may be exposed simultaneously, thus avoiding undesirable artifacts due to the movement of the vehicle, and allowing suppression of daylight by means of short exposure times. Furthermore, this embodiment does not require moving parts.

It will be understood that in all of the examples the measurements may be performed from a moving vehicle where the illuminated area and the observation area move in the longitudinal direction of the road markings in addition to the scanning movement. It is preferred that the longitudinal movement due to the moving vehicle is slower than the scanning speed.

Embodiments of the method and apparatus described herein have mainly been described in the context of road markings. However, it will be appreciated that embodiments of the method and apparatus described herein may also be used to measure retroreflectivity of other surfaces and/or other reflective materials applied to a surface.

For example, it will be appreciated that the apparatus described herein may also be used to detect road studs and to determine the reflectance of road studs. Normally, road studs have a reflecting surface that has a much higher reflectance than normal road markings. Consequently, when a road stud enters the illuminated area used for determining retroreflectivity of road markings, the amount of light reflected from the road stud may be so large that the detector may saturate or at least not provide an accurate measurement. However, due to the high reflectance of the road stud, the system may detect them already on previous images, i.e. when the road stud is still outside the primary illuminated area used for determining retroreflectivity of road markings. This may be due to straylight (e.g. caused by a front plate including light spreding spots) from the apparatus that is reflected from the road stud, or by providing a separate, weaker light source that illuminates a secondary area in front of the measuring device but at a larger distance from the apparatus than the primary illuminated area. Thus, when the road stud enters the secondary area, the device may measure the reflectivity of the road stud. Depending on the size of the observation area and the size of the secondary area, the device may be able to perform a plurality of measurements for each road stud before the road stud enters the primary illuminated area. The distance at which these measurements are taken may subsequently be determined when the road stud is detected in the illuminated area, e.g. from the known time interval between measurements and from the speed of the vehicle carrying the measuring device (e.g. as measured by a GPS device). For example, the detection of the presence of a road stud in the primary illuminated area may trigger the device to correlate images of a road stud in the secondary area of previous exposures/measurements, and thus correlate measured retroreflectivity values with the detected road stud.

In the claims enumerating several means, several of these means can be embodied by one and the same element, component or item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, elements, steps or components but does not preclude the presence or addition of one or more other features, elements, steps, components or groups thereof.

The invention claimed is:

1. An apparatus for measuring retroreflectivity of a surface, the apparatus comprising:
   a light source for illuminating an area of said surface at an incident angle relative to the surface;
   a detector for detecting light reflected back from an observation area of the surface at an observation angle relative to the surface;
   a signal processing unit adapted to receive a detector signal from the detector and to determine, from at least the received detector signal, a measure of the retroreflectivity of at least a part of the surface;
   at least one device for measuring a distance between the apparatus and the illuminated area, the device for measuring a distance between the apparatus and the illuminated area comprising the light source, the detector and the signal processing unit;
   wherein the signal processing unit is further adapted to adjust the measure of the retroreflectivity responsive to the measured distance;
   characterised in that the detector comprises a position-sensitive detector for detecting light as a function of a position within a light receiving area of the detector, wherein the signal processing unit is adapted to determine the distance from a position within the light receiving area of the detected light reflected back from the surface.

2. The apparatus according to claim 1, wherein the detector comprises a 2-dimensional detector adapted to receive an image of the illuminated area of the surface; and wherein the signal processing unit is adapted to determine the distance from a position of the image on the 2-dimensional detector.

3. The apparatus according to claim 1, wherein the signal processing unit is adapted to determine from a captured image of the illumination area the distance between the apparatus and the illuminated area by me of a triangulation operation.

4. The apparatus according to claim 1, further comprising an optical system for directing a predetermined portion of a light beam emitted by the light source to the detector.

5. The apparatus according to claim 1, wherein the signal processing unit is further adapted to perform a compensation of the detected reflected light for ambient light based on a detection of light reflected from the observation area.

6. The apparatus according to claim 1, wherein the observation angle is smaller than the incident angle.

7. The apparatus according to claim 3, wherein the signal processing unit is adapted to determine said distance from a position of a retroreflected stripe of light on the detector, using trigonometric relations.

8. The apparatus according to claim 4, wherein the optical system is configured to direct a predetermined portion of the light beam emitted by the light source to a first position on the light receiving area, and wherein the optical system is further configured to direct at least a portion of the light reflected back from the surface to a second position, different from the first position, on the light receiving area.

9. The apparatus according to claim 5, wherein the signal processing unit is adapted to perform the compensation of the detected reflected light for ambient light based on a detection of light reflected from a portion of the observation area different from the illuminated area.

10. The apparatus according to claim 5, wherein the light source is configured to illuminate the illuminated area by flashes of light leaving the illuminated area unilluminated during an interval between consecutive flashes; wherein the detector is further adapted to detect light reflected back from the observation area during said interval between consecutive flashes; and wherein the signal processing unit is adapted to perform the compensation of the detected reflected light for ambient light based on a detection of light reflected from the illuminated area during said interval between consecutive flashes.

11. The apparatus according to claim 6, wherein the apparatus measures retroreflective property of road markings.

12. The apparatus according to claim 11, wherein the retroreflective property is measured from a moving vehicle.

13. A method for measuring retroreflectivity of a road surface while moving across the road surface, the method comprising:
   providing an apparatus for measuring the retroreflectivity of the road surface while moving across the road surface, the apparatus comprising a light source for illuminating an area of said road surface at an incident angle relative to the road surface and a detector for detecting light reflected back from an observation area of the road surface at an observation angle relative to the surface;

receiving a detector signal indicative of an intensity of light reflected back from the illuminated area of the road surface, and detected by the detector at the observation angle relative to the surface responsive to the illumination of the illuminated area at an incident angle relative to the road surface;

determining, from at least the received detector signal, a measure of the retroreflectivity of the road surface; and receiving from at least one measurement device at least one measurement indicative of a distance between the apparatus and the illuminated area;

wherein determining the measure of the retroreflectivity comprises adjusting the measure of the retroreflectivity responsive to the measured distance relative to a nominal distance.

14. The method according to claim 13, wherein the at least one measurement device is different from said apparatus for measuring the retroreflectivity.

15. The method according to claim 14 further comprising determining an inclination of a vehicle relative to the road surface and computing the distance between the apparatus and the illuminated area from at least the determined inclination.

16. The method according to claim 14, wherein receiving from at least one measurement device comprises receiving a measurement of the distance between the apparatus and the illuminated area from a range finder configured to directly measure said distance; wherein the range finder is separate from the apparatus.

17. An apparatus for measuring retroreflectivity of a road surface, the apparatus comprising:

a light source for illuminating an area of said road surface at an incident angle relative to the surface;

a detector for detecting light reflected back from an observation area of the road surface at an observation angle relative to the road surface;

a signal processing unit adapted to receive a detector signal from the detector and to determine, from at least the received detector signal, a measure of the retroreflectivity of at least a part of the road surface; and at least one device for measuring a distance between the apparatus and the illuminated area, wherein the signal processing unit is further adapted to adjust the measure of the retroreflectivity responsive to the measured distance;

wherein the observation angle is smaller than the incident angle.

* * * * *